United States Patent [19]

Brahme

[11] 4,442,352
[45] Apr. 10, 1984

[54] SCANNING SYSTEM FOR CHARGED AND NEUTRAL PARTICLE BEAMS

[75] Inventor: Anders Brahme, Bromma, Sweden

[73] Assignee: Instrument AB Scanditronix, Sweden

[21] Appl. No.: 356,284

[22] Filed: Mar. 9, 1982

Related U.S. Application Data

[63] Continuation-in-part of Ser. No. 150,447, May 16, 1980, abandoned.

[30] Foreign Application Priority Data

May 17, 1979 [SE]  Sweden .............................. 7904360

[51] Int. Cl.³ .......................... H01S 1/00; G01K 1/08
[52] U.S. Cl. .................................. 250/251; 250/398; 250/399; 250/493.1
[58] Field of Search ................... 250/309, 310, 396 R, 250/398, 399, 493, 298, 251; 313/361

[56] References Cited

U.S. PATENT DOCUMENTS

| | | | |
|---|---|---|---|
| 3,448,263 | 6/1969 | Leboutet et al. | 250/396 R |
| 3,541,328 | 11/1970 | Enge | 250/396 R |
| 3,660,658 | 5/1972 | Leboutet et al. | 250/49.5 D |
| 3,840,743 | 10/1974 | Tamura et al. | 250/307 |
| 4,063,098 | 12/1977 | Enge | 250/396 R |
| 4,066,895 | 1/1978 | Iwanaga | 250/296 |
| 4,081,674 | 3/1978 | Tamura et al. | 250/251 |
| 4,134,017 | 1/1979 | Azam et al. | 250/396 R |

FOREIGN PATENT DOCUMENTS 514341 12/1971 Switzerland .

Primary Examiner—Bruce C. Anderson
Attorney, Agent, or Firm—Lewis H. Eslinger

[57] ABSTRACT

A method and a device for irradiating a confined volume of material, generally situated at a substantial depth below surface, with a beam of high energy charged or uncharged (neutral) particles have a characteristic feature that a beam of charged particles (e.g., electrons, protons, or deuterons) coming from a radiation source is scanned electrically in two orthogonal directions. To obtain a scanned beam of neutral particles, for example photons, a scanned beam of electrons is directed into a target which then emits the scanned beam of neutral particles to be incident into the confined volume. The emerging neutral particles will be emitted from the target predominantly in the direction as the incoming charged particles. The device according to the invention includes a beam optical system arranged in the path of a beam of charged particles emerging from a radiation source and having two magnetic scanning arrangements (1a, b and 5a, b, respectively), each of which causes the particle beam to be scanned in one of two orthogonal planes, so that the scanned beam leaves the second scanning magnet from substantially one and the same effective scanning center for both planes.

12 Claims, 7 Drawing Figures

SCANNING SYSTEM FOR CHARGED AND NEUTRAL PARTICLE BEAMS

This is a continuation-in-part of application Ser. No. 150,447, filed May 16, 1980 abandoned.

The present invention relates to a device for irradiating a confined volume of material, normally situated at a substantial depth within a body by a beam of high energy charged or neutral particles. The charged particles may be protons or electrons, and the neutral particles may be photons or neutrons.

The invention has one possible application in connection with the irradiation of deep-seated tumours.

High-energy electrons and photons have been used in radiation therapy since the fifties. The commonly used radiation modalities involve low to medium energy ranging from a few MeV up to some twenty MeV. These kinds of radiation have been applied also for treating deep-seated tumours although a better therapeutical result may be expected if considerably higher radiation energies were used. The reason that higher energies have not been considered is that several different factors restrict the production and use of high energy electrons and photons having peak energies of some twenty up to some fifty MeV. A limiting factor is that in the market there is no cheap, compact and lightweight accelerator which delivers a sufficiently high radiation energy. Other limiting factors are technical problems which impede the production of therapeutic beams of high quality at these high energies. By high quality it is meant that the particles of the beam as far as possible move in parallel paths, that the beam is monoenergetic, and that the flow of particles is constant across the cross-section of the beam. The last-mentioned property is known as homogeneity or uniformity. In the case of, for example, electron beams, at these high energies one loses the steep dose falloff beyond the therapeudic range otherwise occurring at low energies, particularly when ordinary scattering foils are used for flattening the beam. In the case of photon beams the problem is that very thick flattening filters are needed, which will decrease the effective photon energy so that only modest improvements in beam penetration of the flattened beam are obtained if the energy of the radiation of the original beam is increased.

There exist a number of different proposals how to produce high energy electron beams of high quality and large therapeutic range. Two fundamental problems occur in respect of these beams. The first problem concerns how to provide large homogeneous (flattened) radiation fields. The second problem is how to bring about a deep therapeutic range.

The most common method of obtaining uniform beams is to utilize a single scattering foil. The use of a scattering foil is suitable for energies under 10 MeV and for small radiation field sizes. If greater energies are to be used, the scattering foils become thicker, but such thick scattering foils cause a considerable decrease of the quality of the electron beam. Compared to the amount of material in the particle beam, the well-known technique of using double scattering foils is about 10 times better than a similar technique using a single scattering foil and provides high quality electron beams at energies up to 20 MeV. At still higher energies, however, the electron radiation becomes further degraded, even if two foils are used which are about 10 times thinner than those utilized with the single foil technique. At the very highest energies from about 25 MeV to about 50 MeV, electromagnetic systems using defocusing or mechanically scanned magnets or quadrupoles are the only ones known up to now for providing high quality beams. Compare, e.g., Swiss Pat. No. 514,341 (U.S. Pat. No. 3,660,658) and U.S. Pat. No. 4,063,098. However, in practice, these electromagnetic systems have various technical problems associated with them and they can not be used to produce broad uniform photon beams.

It is known that a deep therapeutic range may be achieved by using mechanically moved deflection magnets by means of which a quadratic decrease of the radiation flow with the distance changes to a linear decrease. This increases the therapeutic range of the beam since the dose decrease becomes less steep.

Another method in which a similar technique is used is the so-called pendular technique which is utilized in combination with flat or fan-shaped beams from certain betatrons. However, corresponding results can be obtained with most conventional treatment units simply by irradiating the volume (tumour) with a multitude of parallel or convergent beams. In the transition to a continuum of fields of various directions (dynamic radiation therapy) the geometric dose decrease may even be transformed into a hose increasing with depth.

Various methods have been proposed to produce broad uniform photon beams. For high-energy photon beams the choice of material for the so-called target and for the flattening filter is of fundamental importance. Two different methods have been proposed to produce such high-energy photon beams. One method uses a target and a flattening filter made of a material having a low atomic number for generating a beam having the highest possible photon energy and the greatest possible penetration along the central axis of the beam. The other method involves the use of a target the material of which has a medium atomic number and a flattening filter composed of a high atomic number material in the center and a low atomic number material at the periphery, a high quality photon beam of high homogeneity at all depths and field sizes being generated due to simultaneous, homogeneous radiation fluence and mean photon energy. The first method achieves deeply penetrating narrow beams at the cost of a variation in the homogeneity of the beam with depth for broad beams. The second method involves the production of uniform beams practically independent of field size and depth, but this takes place at the cost of a reduced penetration depth at small field sizes.

The present invention aims at providing a simple and reliable device for irradiating a confined volume of material, generally at a substantial depth, with a beam of high energy charged or neutral particles combining the respective advantages of the two above-mentioned methods.

For most practical purposes it is important that the radiation source is of small extent. Such a radiation source is realized by means of a beam optical system according to the invention. This beam optical system includes two scanning magnets each of which causes the particle beam to be scanned in one of two orthogonal planes, the beam scanned in each of the planes leaving the associated scanning magnet from an effective scanning centre. Furthermore, the beam optical system includes a deflection magnet disposed between the scanning magnets for deflecting the path of the beam in space. By utilizing the beam optical properties of the deflection magnet in such a way that the deflection magnet produces an image of the effective scanning center of the first scanning magnet, as seen in the beam direction, at a point which coincides with the effective scanning center of the second scanning magnet, as seen in the beam direction, the beam scanned in two orthogonal planes will radiate isotropically from the scanning centre of the second scanning magnet. By using the deflection magnet in this way a compact scanning system having a negligible distance between the scanning centers of the two scanning magnets is obtained.

The beam optical system according to the present invention also enjoys the advantage that a well-defined distance between the radiation source (i.e., the scanning centre of the second scanning magnet) and the surface under which the said confined volume of material is situated is obtained. This distance is the so-called SSD-distance (source-to-surface distance). The beam emerging from the beam optical system can be described as nearly a point isotropic beam with the same intensity and energy distribution in all directions. In addition, due to the simple dipole scanning magnets used, the distortion of the elementary (non-scanned) beam will be considerably less than if quadrupoles were used to scan the beam in both planes.

The beam optical system according to the present invention is of particular interest, since the second (last) scanning magnet, as seen in the beam direction, can be made very strong and short, whereby a bremsstrahlung-producing target can be placed near the effective scanning center of the last scanning magnet and thus transform the scanned electron beam into a scanned photon beam. A corresponding technique is used for transforming a proton beam into a flattened neutron beam by using a scanning system according to the invention. Also a deuteron beam can be transformed into a flattened neutron beam scanned according to the invention. The technique here is particularly important, not least owing to the fact that broad, uniform photon beams or neutron beams, respectively, of any energy may be produced without having to use thick flattening filters. Furthermore, the photon spectrum will be improved when the otherwise degrading filter is now omitted and the hard photon spectrum pointed forward is distributed isotropically across the whole radiation field.

The photon beam generated in this way will accordingly combine the advantages of the two conventional methods mentioned above, i.e., high penetration and high homogeneity, yet without being encumbered by the disadvantages of these known methods. In addition, the scanned photon beam now proposed will increase the available dose, since no flattening filters of a conventional kind are needed. Such flattening filters absorb as much as 50 to 80% (depending on the energy of the radiation) of the photon fluence. Owing to this fact, radiation shielding problems outside the field will be decreased by a factor of at least 2 to 5. Still more important is that the neutron production in the flattening filter and in fixed collimators will then also decrease by the same factor of 2 to 5. Consequently, by utilizing the scanned photon beam according to the invention the neutron shielding can be decreased to a corresponding degree.

Swiss Pat. No. 514,341 relates to a system wherein the beam is scanned in two orthogonal planes. An attendent drawback with the known system is that it requires a quadrupole triplet with a wide aperture to focus the beam. This arrangement increases the cost and length of this system, especially for higher energies. Further, the pole gap of the deflection magnet must be wide since the first deflection magnet is scanning the beam in a plane which is perpendicular to the deflection plane of the deflection magnet. In addition, the exciting current of the large deflection magnet is varied to scan the beam in the deflection plane, which further complicates this magnet. In accordance with the present invention, a considerably simpler, separate scanning magnet allowing a much higher scanning speed is used.

U.S. Pat. No. 4,063,098 relates to a system scanning the radiation beam in a plane which is perpendicular to the deflection plane of the deflection magnet. This has the same disadvantages as described above in conjunction with the above Swiss patent. In addition, the beam is scanned only in one plane.

The invention will be described in more detail below in connection with the attached drawings, in which.

Figure 1:
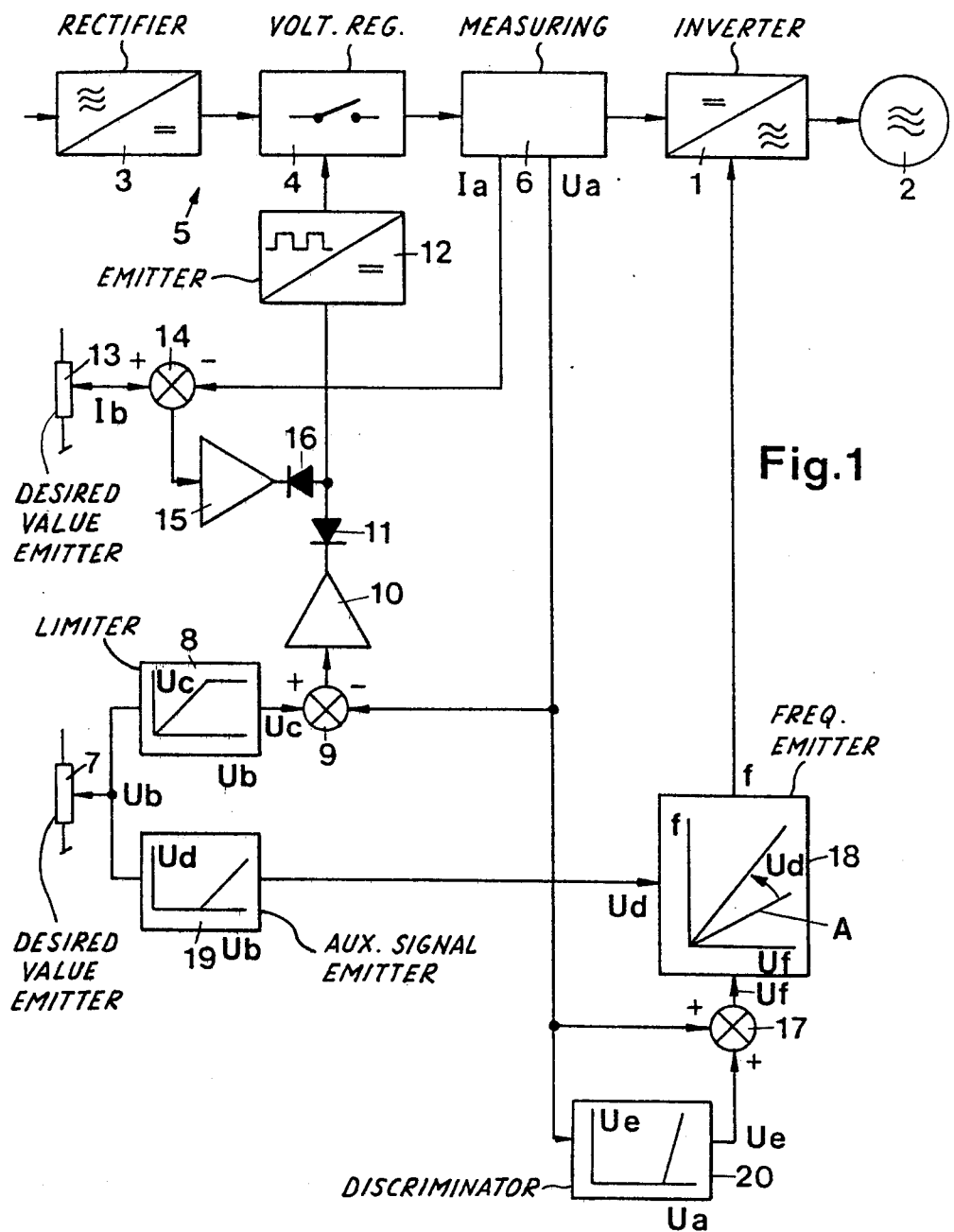
FIG. 1 is a diagrammatic side view of a beam optical system according to a preferred embodiment of the invention.

FIGS. 5 and 6 are diagrams showing isodose graphs of the volume of material irradiated with electrons (FIG. 5) and photons (FIG. 6); and FIG. 7 shows the distribution of the absorbed dose transversely of the irradiated volume when irradiating with one (graph 1) and two (graph 2) showers of particles (i.e., particle pulses) in the border area of the beam field.

An embodiment of this invention is explained with reference to FIGS. 1 and 2.

From a source S of high energy electron radiation there emanates an electron beam $e^-$. The energy of the electrons is of the order of 1 to 50 MeV. The electron beam $e^-$ is led into a beam optical system including two scanning magnets 1a, b and 5a, b, respectively, and a deflection magnet 3a, b placed therebetween. The scanning magnet 1a, b includes two pole faces 1a, 1b of an electromagnet (not shown). By varying the electric current to each electromagnet and thereby accordingly varying the magnetic field in the gap between the pole faces, the electron beam $e^-$ may be deflected to a varying degree in the plane of the drawing, for example between the extreme positions indicated by full lines. The beam emerges from the scanning magnet 1a, b as if it came from an effective scanning center 2. The beam scanned in the plane of the drawing is then deflected in a deflection magnet 3a, b which in the case illustrated deflects a central particle beam 90°. The deflection magnet is of a conventional type with two mutually perpendicular pole edges which intersect at the point 4. The beam emerging from the deflection magnet thereupon passes through a second scanning magnet 5a, b similar to the first-mentioned scanning magnet 1a, b. The pole faces 5a, 5b of the second scanning magnet are oriented at right angles to the pole faces 1a, b. The magnetic field between the pole faces 5a, b is varied by feeding the corresponding electromagnet with another varying electric current. The beam emerging from the scanning magnet 5a, b will thus leave the scanning magnet as if it emerged from an effective scanning center 6. The beam leaving the second scanning magnet 5a, b is scanned in a plane which is perpendicular to the plane of the drawing. The deflection magnet 3a, b forms an image of the scanning center 2 at a point which coincides with the scanning center 6. This is effected by locating the point 4 on the straight line 7 which connects the scanning centers 2 and 6 with each other. By this arrangement the scanned beam will radiate isotropically from the scanning center 6.

By applying suitable varying scanning voltages to the respective electromagnets the electron beam may be caused to travel across the entrance surface of the volume to be irradiated. By making the pole faces 5a, b short and the field strength thereof high the length of the second scanning magnet may be shortened. If a target 8, for example of tungsten with a thickness of about 2 mm., as seen in the beam direction, is positioned behind and close to the scanning center 6 of the electron beam, the latter is transformed into a photon beam which likewise radiates almost isotropically from the scanning center 6.

Figure 3:
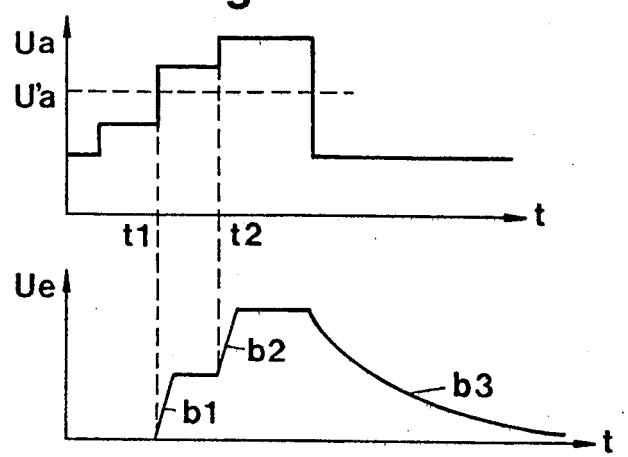
FIGS. 3 and 4 are diagrams showing the depth dose distribution in the volume of material irradiated with electrons (FIG. 3) and photons (FIG. 4)
Figure 4:
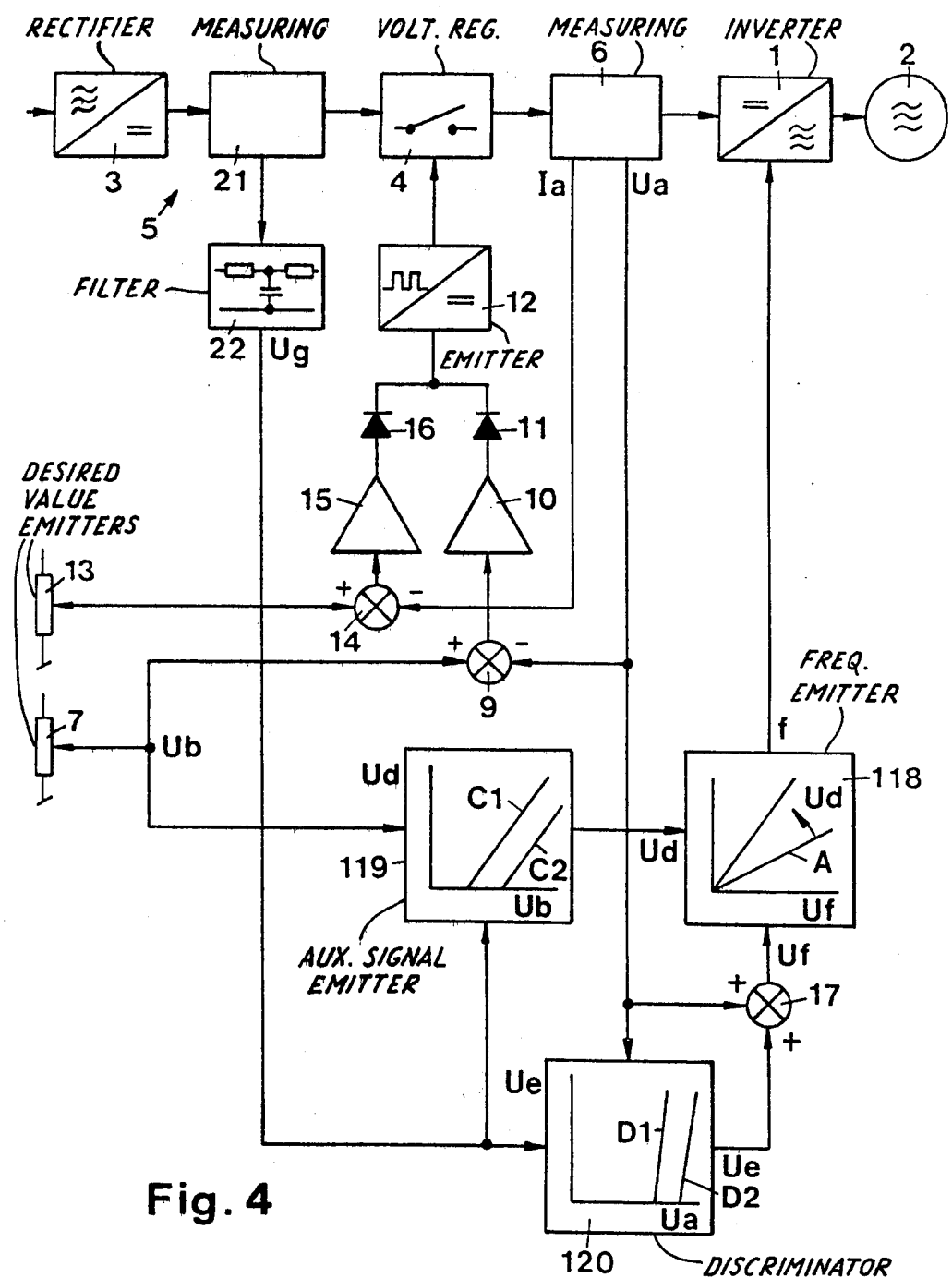

It is also possible to replace the target 8 by a thin target, i.e., a so called transmission target, whereby the beam which leaves the scanning center 6 will contain both photons and electrons. A cleaning magnet 9 may also be added below the transmission target to remove the charged particles that are transmitted and leave a clean beam of neutral particles. FIGS. 3 and 4 show the depth dose distribution in the volume of material irradiated with electrons and photons, respectively. In this case, the material is a volume of water. The full line graph in FIG. 3 shows the depth dose distribution of a crude, unflattened electron beam with the energy 45.6 MeV which hits the water surface from a 100 cm. distance. The effective diameter of the beam is 9.1 cm. The dotted graph in FIG. 3 shows the depth dose distribution of a beam which has been scanned according to the present invention and which thus from the scattering center 6 radiates isotropically towards a water surface. The source-to-surface distance (SSD) is 100 cm. Accordingly, in this case the effective diameter of the beam is infinitely large. As is apparent, the dose is larger at great depths than is the crude unflattened beam.

The graph marked along with long dashes in FIG. 4 shows the depth dose distribution of photons with the energy 50 MV which pass through a conventional 4 cm. thick flattening filter of lead. Without this flattening filter the depth dose distribution would have the graph shown by a full line. If a flattening filter of titanium having a thickness of 4 cm. is utilized, a depth dose distribution is obtained corresponding to the graph marked with short dashes. If the electron beam is scanned according to the invention and if a target 8 of 1 mm. tungsten is utilized (beryllium could also be used), a depth dose distribution of the kind marked with the dotted graph is obtained. It is evident that the dose maximum is located substantially deeper (about 4 cm. deeper) if the scanning technique according to the present invention is utilized.

Normally, the beam from the radiation source S is not continuous but is delivered in the form of pulses of short duration, each pulse comprising several millions of particles and referred to as a particle shower. With the scanning technique of the present invention it is possible to control the scanning pattern and the position of the individual particle showers.

FIG. 5 illustrates an isodose diagram of an individual electron pulse which can be scanned stepwise according to an arbitrary pattern. The energy of the electrons is 50 MeV. As is apparent from FIG. 5 the radiation dose is concentrated to a small surface area at the entrance point on the surface of the irradiated object, in this case a volume of water, while the cross-section of the radiation dose spreads in pear shape with increasing depth and only after the beam has penetrated the surface. Experimental results show that the concentrated radiation dose in the small surface area brings about diminished skin reaction owing to the presence of surrounding non-irradiated skin tissue.

The pattern according to which the beam is scanned is run through once and the periods of the individual beam pulses, or particle showers are made very short so that the whole local radiation dose is administered in a single particle shower (pulse) of very high dose rate (FIG. 5). Due to the fact that the period of irradiation then becomes short, advantageous biological reactions are obtained when irradiating tissues.

FIG. 6 shows isodose graphs corresponding to FIG. 5 recorded for a photon beam with the energy 50 MeV, which has been scanned across a water surface and has delivered the entire local dose in a single pulse. The abscissa and ordinate respectively represent penetration depth and lateral deviation.

By scanning the beam stepwise in at least one of the orthogonal planes and by controlling the length of each step in proportion to the dose contribution of the immediately preceding particle shower, one may compensate for short term variations of the intensity of the radiation emerging in each pulse. By correlating the length of the step against the intensity of the preceding particle shower the ratio of the mean value of the dose which is delivered to the irradiated volume becomes constant. When scanning stepwise, an extra pulse (particle shower) may be delivered to the extreme border area to improve the dose distribution across the irradiated volume. FIG. 7 illustrates this technique. The figure shows one quadrant of the radiation field. The volume is irradiated with 7×7 pulses each placed at a distance of 5 cm. from its nearest neighbours. One pulse each is accordingly delivered at each scanning point 0, 5, 10, and 15 cm. from the center of the square, respectively. As will be seen, the dose decreases in the border area, i.e. about 15 cm. from the center. By now instead delivering two pulses when the beam is in its extreme position, counting from the center, the dose distribution is considerably improved, which is seen from the graph 4. The graph 1 shows the dose distribution in the case where only one pulse is delivered at each point. Thus by increasing the pulse density a uniform absorbed dose is achieved over all of the irradiated volume.

Although various well-defined scanning techniques have been described above, the irradiation may of course take place by allowing the beam to run freely, for example in a meander-shaped pattern, across the surface to be irradiated. The scanning of the beam may also be carried out stepwise in two orthogonal planes in such a way that the scanned beam follows a scanning pattern which, line-by-line, follows the crossing points of a lattice, which brings about so-called grid or sieve therapy. This method is of great interest particularly to reduce the skin reaction in the treatment of deep-seated tumors.

Figure 2:
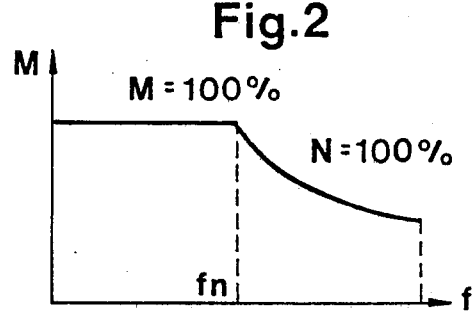
FIG. 2 is a front view of the beam optical system according to FIG. 1.

Notwithstanding that FIGS. 1 and 2 show the use of a deflection magnet 3a, b which deflects at 90°, other deflection angles may of course be used. The pole edges of the deflection magnet should intersect at a point which is located on the straight line 7 which connects the scanning centers 2 and 6 of the scanning magnets with each other. In clinically useful systems of high energies the electron beam will probably have to be deflected, for which reason normally a deflection magnet is needed. The same radiation optical function may be obtained with a quadrupole system or some other beam optical component.

The embodiments of the invention described above can be modified and varied in many ways within the scope of the basic conception of the invention.

I claim:

1. A method of irradiating a confined volume of material normally located at a substantial depth below a surface with a beam of high energy particles, comprising the steps of electromagnetically scanning the beam in a first plane such that the scanned particles emanate from a first center of divergence; forming an image of the first center of divergence of the scanned beam by electromagnetically bending the beam through a spatial angle; and electromagnetically scanning the electromagnetically bent beam in a second plane perpendicular to the first plane with the so-scanned particles emanating from a second center of divergence, and with the second center of divergence being disposed so as to generally coincide with the image of the first center of divergence.

2. A method in accordance with claim 1, including the step of scanning the beam once over said surface in accordance with a predetermined pattern and administering a respective local dose at each of a plurality of points on said surface, each such dose originating from generally one single pulse of radiation.

3. A method of accordance with claim 2, including the steps of scanning the beam step-wise and controlling the length of each step depending on the dose of the immediately preceding administered radiation pulse in order to compensate for short term variations of the intensity of the beam pulses emerging from the radiation source.

4. A method in accordance with claim 2, including the step of scanning the beam over said surface in accordance with a lattice pattern and administering a pulse of radiation at each crossing point of the lattice pattern.

5. A method in accordance with claim 2, including the step of increasing the pulse density along a border area of the volume to be irradiated in order to achieve a uniform absorbed dose over all of the interior of the irradiated volume.

6. Apparatus for irradiating a confined volume of material normally located a substantial distance below a surface, comprising a radiation source emitting a beam of high energy particles and a beam optical system arranged in said beam, said beam optical system comprising a first scanning magnet, a deflection magnet having a deflection plane, and a second scanning magnet; the first scanning magnet having a scanning center from which the scanned beam apparently emanates scanning the beam in the deflection plane of the deflection magnet, the second scanning magnet having a scanning center and scanning the scanned and deflected beam in a plane perpendicular to the deflection plane, with the deflection magnet being so located relative the first and second scanning magnets that the scanning center of the first scanning magnet is imaged generally at the scanning center of the second scanning magnet by means of the deflection magnet.

7. Apparatus according to claim 6, wherein the high energy particles are selected from the group consisting of electrons, protons, and deuterons and a target is placed close to the scanning center of the second magnet to generate as neutral particles, photons and neutrons respectively.

8. Apparatus according to claim 7, wherein the target is a thin foil of tungsten or beryllium.

9. Apparatus according to claim 6, wherein the high energy particles are selected from the group consisting of electrons, protons, and deuterons and a transmission target is placed close to the scanning center of the second scanning magnet, thereby creating a beam of photons radiating isotropically from the scanning center of the second scanning magnet below which a cleaning magnet is placed to remove those charged particles that have penetrated the target.

10. Apparatus in accordance with claim 6, wherein the scanning centers of the first and second scanning magnets and the point at which pole edges of the deflection magnet would, if extended, intersect, all lie along the same straight line.

11. Apparatus in accordance with claim 5, wherein the deflection angle of the deflection magnet is generally 90°.

12. Apparatus in accordance with claim 7, wherein the scanning centers of the first and second scanning magnets and the point at which pole edges of the deflection magnet would, if extended, intersect all lie along the same straight line.

* * * * *